United States Patent [19]

Carroll et al.

[11] Patent Number: 5,503,025
[45] Date of Patent: Apr. 2, 1996

[54] ALIGNMENT EXTENSIOMETER WITH DOUBLE COMPRESSION FITTINGS

[75] Inventors: Norman L. Carroll, Butler; Willard L. Pearce, Allison Park, both of Pa.

[73] Assignee: Applied Test Systems Inc., Butler, Pa.

[21] Appl. No.: 114,519

[22] Filed: Sep. 1, 1993

[51] Int. Cl.[6] .................................................. G01N 3/02
[52] U.S. Cl. ................................................. 73/856; 73/790
[58] Field of Search ............................ 73/849, 856, 826, 73/788, 831, 849, 853; 33/712, 787, 790, 645, 520, 533, 644

[56] References Cited

FOREIGN PATENT DOCUMENTS 2534683  4/1984  France ................................. 33/790

Primary Examiner—Richard E. Chilcot, Jr.
Assistant Examiner—James M. Olsen
Attorney, Agent, or Firm—Daniel W. Ernsberger

[57] ABSTRACT

An alignment extensiometer is shown which attaches to a material testing sample by means of a hinged split cross head and a movable split insert. The extensiometer is used to reduce sample damage and set up time.

2 Claims, 1 Drawing Sheet

ALIGNMENT EXTENSIOMETER WITH DOUBLE COMPRESSION FITTINGS

BACKGROUND OF THE INVENTION

Alignment extensiometers are used with materials testing apparatus to measure the bending strain on the sample. Prior alignment extensiometers measure bending by using four linear displacement transducers to measure the distance between two cross heads attached to the sample. The cross heads are attached to the sample by use of a vice like action to press an insert against the sample. This is a cumbersome process and is prone to jamming and sticking of the insert into the cross head.

Prior inventions have been used to measure bending strain on a dummy sample while the load train is aligned The extensiometer is then removed and the dummy sample replaced with the test sample.

The present invention can be used on test samples to reduce the bending strain and, if desired, to subject the sample to a known bending strain.

SUMMARY OF THE PRESENT INVENTION

According to the preferred embodiment of the present invention, the alignment extensiometer consists of two disc shaped cross heads removably attached by double compression fittings to the sample above and below the gage length. In this preferred embodiment of the invention a split insert is pressed against the sample by closure of the hinged cross head. Four separate linear displacement transducers with movable shafts are equally spaced around the test sample and removably fixed to one of the cross heads so as to measure the distance between the two cross heads. Together the transducers measure the bending strain in the sample.

The present invention eliminates the need for dummy samples and assures alignment without disturbance of the load train. It allows for alignment compensation directly on the specimen and quick assembly and disassembly. The present invention also permits the controlled misalignment of the pull rods when it iS desired to test samples under banding strain conditions.

GENERAL DESCRIPTION OF THE DRAWINGS

DETAILED DESCRIPTION OF THE INVENTION

The present invention can be used with many different types of testing apparatus.

Figure 1:
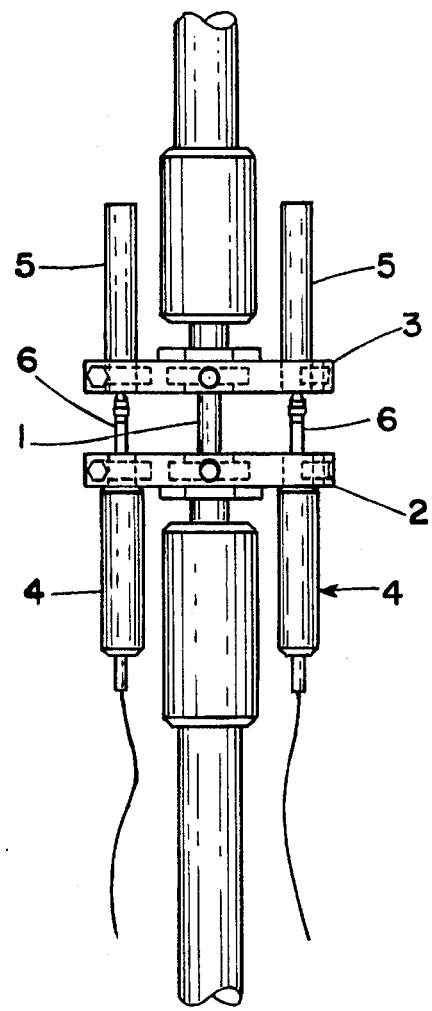
FIG. 1 is a front view of the sample, pull rods and alignment extensiometer.

FIG. 1 shows an alignment extensiometer in its position removably attached to the sample, 1. The alignment extensiometer consists of a lower cross head, 2, an upper cross head 3, and four variable capacitance linear displacement transducers, 4. The preferred transducers are found in U.S. Pat. No. 4,914,543. The four transducers, 4, are removably attached to the lower cross head, 2, and four gage cylinders 5 are removably attached to the upper cross head, 3. It is preferred that the diameter of the gage cylinders, 5, be the same as the diameter of the transducers so that the upper and lower cross head, 2 and 3 are interchangeable. The cross heads 2 and 3 are attached to the sample and oriented with respect to one another so that each shaft, 6, rests on the opposing gauge cylinder 5. This design permits the gauge cylinders, 5, to be advanced through the upper cross head until it touches the shaft of the transducer so as to accommodate any limitation in the travel of the shaft.

Figure 2:
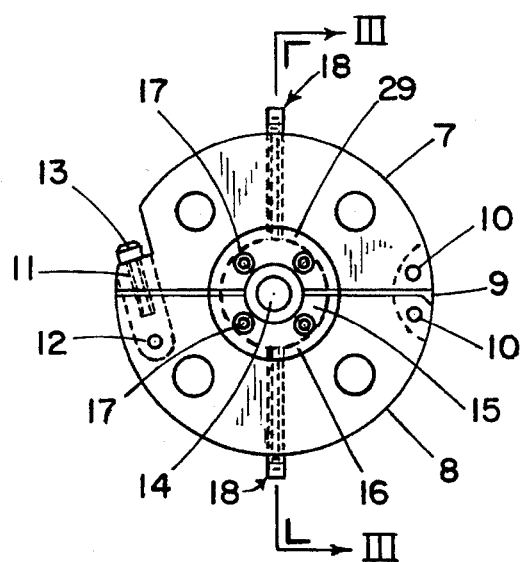
FIG. 2 is an end view of the cross head.
Figure 3:
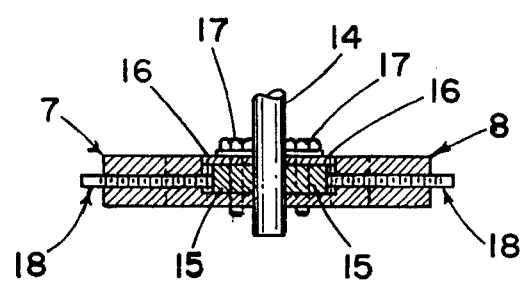
FIG. 3 is a cut away side view of FIG. 2 with hinge and hinge pin not shown.

FIGS. 2 and 3 show a cross head which is split in two parts, 7 and 8 and hinged, by a pivot arm, 9, and two dowel pins, 10, so that when the hinge is closed and locked in place with a pivot arm, 11, secured by a pivot pin, 12, and swivel nut, 13, the sample, 14, can be compressed against the two parts . Sample sizes and shapes vary, so the preferred design makes use of a split insert, 15, that is shaped to fill the space between the sample, 14, and the two parts of the cross head, 7 and 8. The split insert, 15, is fixed to the two parts, 7 and 8 by compression plates, 16 and 29 axial compression screws, 17. When the two parts are closed and locked in place about the sample the cross head becomes fixed to the sample by compression of the insert against the sample. If necessary, two axial compression screws 18 can be advanced thus pushing the split insert, 15 firmly against the sample 14 and the axial compression screws, 17 tightened.

We claim:

1. An alignment extensiometer comprising:

an upper split and hinged disc with a centrally located split insert, compression means for removably fixing the split insert within the plane of the disc, and hinge means for pressing the portions of the split insert against a centrally located sample, a lower split and hinged disc with a centrally located split insert, compression means for removably fixing the split insert within the plane of the disc, and hinge means for pressing the portions of the split insert against the centrally located sample, four linear displacement transducers with movable shafts equally spaced around the sample and removably fixed to the lower disc so that the shaft of each transducer engages the upper disc.

2. The alignment extensiometer of claim one wherein the means for pressing the portions of the split insert against a centrally located sample further comprises a screw radially directed and threadedly engaged in the disc and fashioned to engage the split insert.

* * * * *